United States Patent [19]

Rehmeyer et al.

[11] Patent Number: 5,783,147
[45] Date of Patent: Jul. 21, 1998

[54] APPARATUS FOR AND METHOD OF STERILIZING MEDICAL AND LABORATORY DEVICES AND CLEANING CONTAMINANTS FROM CONTACT LENSES

[76] Inventors: Theodore H. Rehmeyer, 3411 Scarborough Dr., Winston-Salem, N.C. 27106; James R. Shultz, 1267 Wiltshire Rd., York, Pa. 17403

[21] Appl. No.: 680,988

[22] Filed: Jul. 16, 1996

Related U.S. Application Data

[63] Continuation-in-part of Ser. No. 297,125, Aug. 29, 1994, abandoned.

[51] Int. Cl.⁶ ............................................. A61L 2/02
[52] U.S. Cl. ...................... 422/22; 422/293; 422/300; 134/42; 134/901
[58] Field of Search ...................... 422/22, 23, 293, 422/301, 300, 105; 134/1, 42, 901; 204/180.1, 299 R

[56] References Cited

U.S. PATENT DOCUMENTS

5,292,372  3/1994  Swaisgood et al. .................. 134/42 X
5,302,345  4/1994  Oksman et al. ....................... 422/22 X
5,368,708  11/1994  Pankow ................................ 422/22 X

*Primary Examiner*—Robert J. Warden
*Assistant Examiner*—Elizabeth Dawson

[57] ABSTRACT

Apparatus for and method of sterilizing medical and laboratory devices and cleaning contaminants from contact lenses at low voltages, the apparatus including a housing carrying a sterilizing and cleaning well, electrodes, appropriate controls and a power source and the method comprising the steps of positioning a contact lens and an adsorbent so that the adsorbent is disposed between the contact lens and an electric current source, immersing the contact lens, the adsorbent, and the current source in a saline or other appropriate solution, and then applying electric current from the power source through the adsorbent and only over the surface of the contact lens so that contaminants carried by the contact lens migrate to the adsorbent.

24 Claims, 7 Drawing Sheets

APPARATUS FOR AND METHOD OF STERILIZING MEDICAL AND LABORATORY DEVICES AND CLEANING CONTAMINANTS FROM CONTACT LENSES

This is a continuation-in-part application of application Ser. No. 08/297,125 filed Aug. 29, 1994, now abandoned.

BACKGROUND OF THE INVENTION

1. Field of the Invention

The present invention relates generally to sterilizing medical and laboratory devices and to sterilizing and cleaning contact lenses and more particularly to an apparatus for sterilizing medical and laboratory devices and an apparatus and method for cleaning contaminants from contact lenses.

2. Description of the Prior Art

Sterilization of medical instruments used in the offices of doctors, dentists and veterinarians and of equipment used by laboratories is usually accomplished by the use of autoclaves wherein those items are subjected to intense heat to kill all bacteria that may be associated with them. Autoclaves come in varying sizes to accommodate instruments of varying sizes and are sometimes complex and usually expensive. Utilizing such sterilization equipment involves high power consumption as well as lengthy time exposure of the instruments within the equipment to assure complete sterilization.

In some instances, equipment of this nature can be cleaned chemically by spraying with appropriate disinfectants to remove bacteria associated therewith. Again, the compounds utilized to effect such cleaning are expensive and involve lengthy procedures during their application to again ensure complete sterilization of the devices.

Contact lenses present a unique medical or healthcare device which require sterilizing and cleaning on a regular basis in order to ensure continued effective and comfortable use. The presence of contaminants on the surface of such lenses directly affect the comfort and utilization of these objects. Most of these contaminants are proteins produced by the eyes, tear ducts, and eyelids for lubrication and protection of optic tissues. These materials accumulate on the surface and interior of the lens to form microscopic protrusions which irritate and inflame the cornea and eyelid, thereby causing discomfort.

Several methods of removing these contaminants have been used including washing the accumulated protein from the lens surface with a mild detergent and utilizing a solution of proteolytic enzyme which digests the protein molecules. Neither have been totally satisfactory since the detergents can damage the lens and the proteolytic enzyme solution fails to obtain complete protein removal.

In U.S. Pat. No. 4,921,544 (Cowle et al.), the contact lens is placed in an electrophoretic solution within a container and an electric field is applied to the solution through two electrodes in the solution which causes charged protein molecules attached to the lens to migrate to the oppositely charged electrodes. While this method represents an improvement in the art, proteins migrating to the electrode must overcome a diffusion gradient created by the migration which tends to drive proteins from the electrode into the solution and thereby permits some of the free proteins to return to the lens.

In U.S. Pat. No. 4,872,965 (Pankow), electrodes are immersed in solution baths external to the lens, and current is provided to the lens by a transmission means which rests on the lens surface. Application of the electrical current causes contaminants to migrate from the center of the lens to its surface. From this point, the contaminants are then removed from the lens surface or from the electrochemical transmission means by wiping.

Thus, while instrument sterilization has been effetively utilized over the years, there is a continued need to develop procedures within sterilizing such instruments with less expensive equipment and for shorter durations of time. Moreover, numerous methods have been utilized to accomplish contact lens cleaning, and though improvements have been made, there is still a need for improvement to provide more thorough cleaning and to avoid wearer discomfort associated with the process. It is to these needs that the present invention is directed.

OBJECTIVES AND SUMMARY OF THE INVENTION

It is an objective of the present invention to provide an apparatus for sterilizing medical devices and laboratory equipment utilizing low voltages and low current flow at levels not previously believed to be feasible.

A further objective of the present invention is to provide an apparatus for sterilizing medical and laboratory devices utilizing a cleaning well, electrodes and a power source which is simple in construction and economical to use.

Another objective of the present invention is to provide an apparatus for cleaning contaminants from contact lenses utilizing a cleaning well, electrodes, controls and a power source and which can be made small enough to be carried conveniently by the user as a portable device.

A further objective of the present invention is to provide a method of cleaning contaminants from contact lenses which overcomes the problems associated with the equilibrium of electrochemical and diffusion gradients.

It is yet another objective of the present invention to provide an electroblotting method of cleaning contact lenses which eliminates the need for wiping protein from the lens after the application of electric current.

Yet still another objective of the present invention is to provide a simple, inexpensive, and easily manufactured apparatus for commercial production and to utilize a simple and uncomplicated method for operating such device.

These objectives and others are satisfied by the present invention which is in part an apparatus for sterilizing medical and laboratory devices at low voltages, in part an apparatus for sterilizing and cleaning contaminants from contact lenses at low voltages, and finally an apparatus and method of cleaning contaminants from contact lenses by positioning the lens, an adsorbent and power source so that the adsorbent is disposed between the contact lens and the power source and so that current passes only over the surface of the lens. In the sterilizing apparatus, current is dispersed through a solution, which can be any known saline or other suitable solution for cleaning; however, the concentration of current is shaped by the electrodes in a path available to the current to flow between the electrodes. Current flow carries the charged protein articles carried by the lenses toward the oppositely charged electrodes which path forces the proteins to encounter the adsorbent where they are captured and removed.

Thus there has been outlined, rather broadly, the more important features of the invention in order that the detailed description that follows may be better understood and in order that the present contribution to the art may be better appreciated. There are obviously additional features of the invention that will be described hereinafter and which will form the subject matter of the claims appended hereto. In this respect, before explaining several embodiments of the invention in detail, it is to be understood that the invention is not limited in its application to the details of construction and to the arrangement of the components set forth in the following description. The invention is capable of other embodiments and of being practiced and carried out in various ways.

It is also to be understood that the phraseology and terminology herein are for the purpose of description and should not be regarded as limiting in any respect. Those skilled in the art will appreciate the concept upon which this disclosure is based and that it may readily be utilized as a basis for designing other structures, methods and systems for carrying out the several purposes of this development. It is important that the claims be regarded as including such equivalent constructions insofar as they do not depart from the spirit and scope of the present invention.

Thus the enumerated objectives and others identified hereinafter along with the various features of novelty which characterize the invention, are pointed out with particularity in the claims annexed to and forming a part of this disclosure. For a better understanding of the invention, its operating advantages and the specific objects obtained by its use, reference should be made to the following detailed description taken in conjunction with the accompanying drawings.

DETAILED DESCRIPTION OF THE INVENTION

Figure 1:
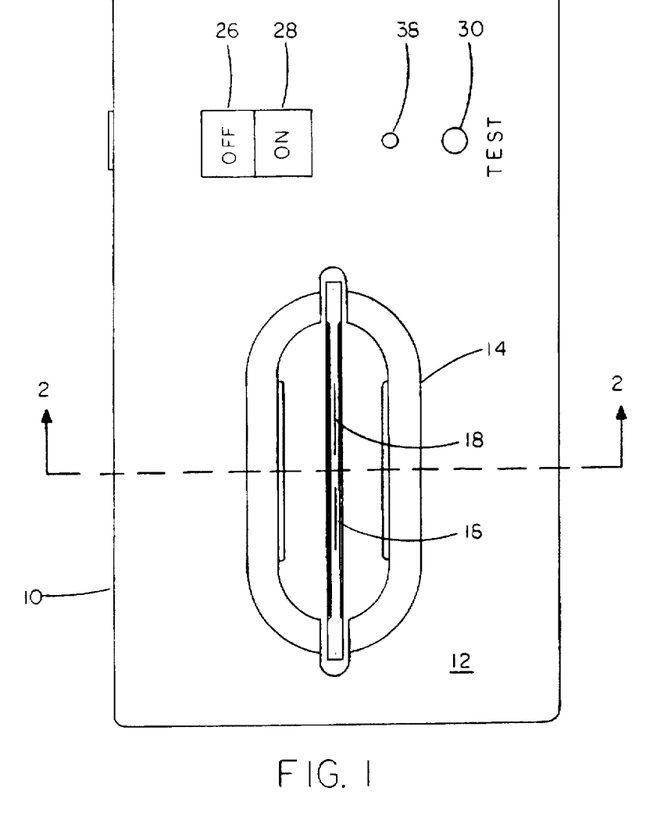
FIG. 1 is a plan view of one embodiment of an apparatus for cleaning contaminants from one or more contact lenses comprising the present invention.

Referring now first to the apparatus for cleaning lenses and particularly to FIG. 1, the apparatus includes a housing shown generally as 10 having within its upper surface 12 a cleaning well 14 which is configured to accommodate and support one or more adsorbents or filters 16 between which are positioned lenses 18 to be cleaned. Well 14 functions to hold these elements by having a lower recessed portion 20 and offers easy access for the user by reason of an expanding upper portion 22 sufficiently wide to accommodate the user's two fingers holding and subsequently inserting and removing adsorbent holder 46, adsorbent 16 and lens 18.

Figure 2:
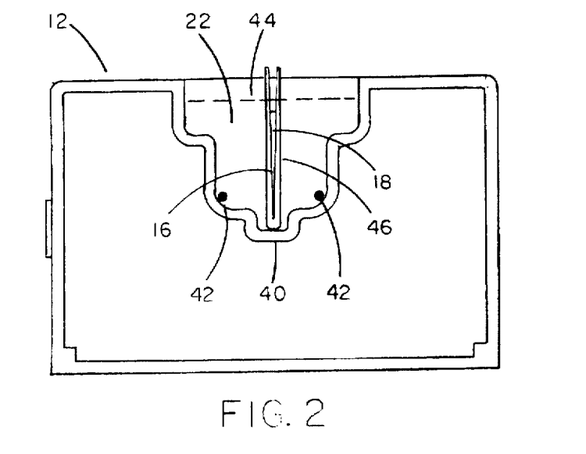
FIG. 2 is an end elevational sectional view of the apparatus of FIG. 1 taken along line 2—2 in which has been positioned two contact lenses and an adsorbent.
Figure 3:
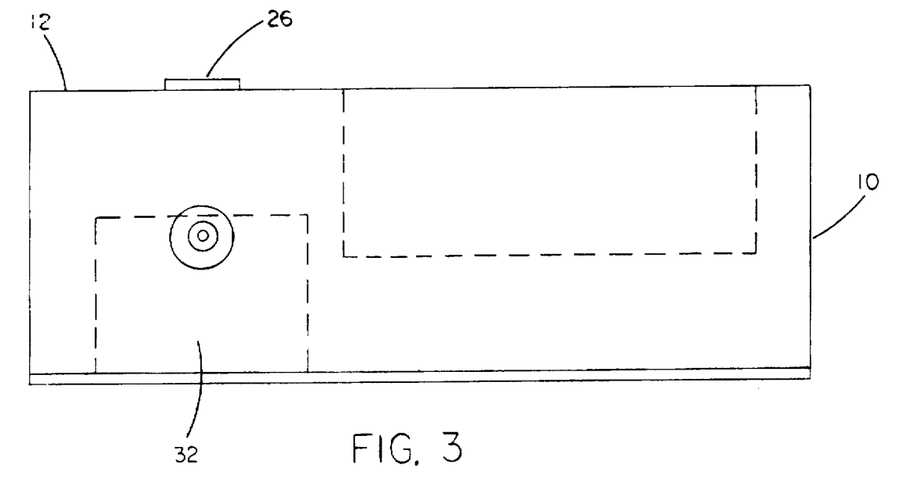
FIG. 3 is a side elevational sectional view of the device shown in FIGS. 1 and 2.
Figure 4:
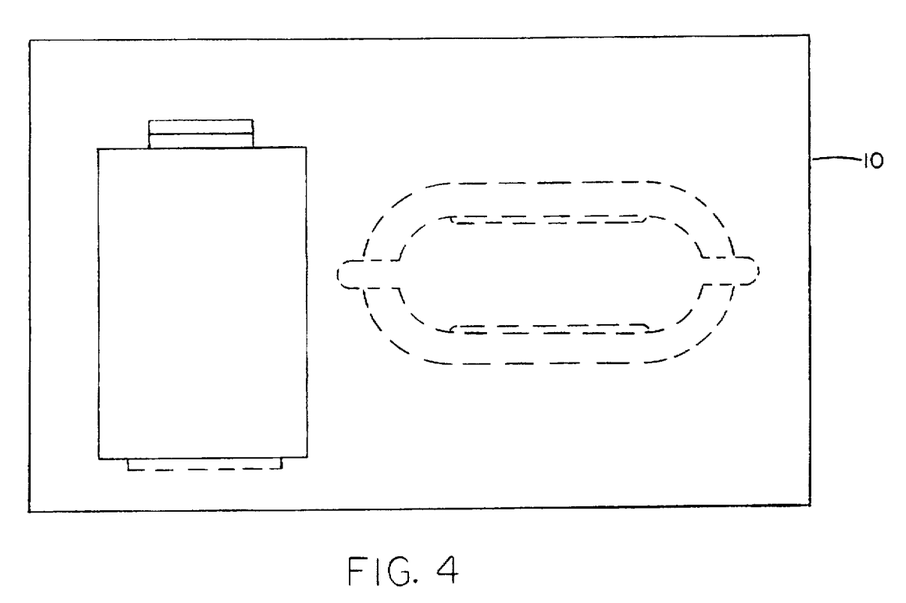
FIG. 4 is a bottom view of the device shown in FIGS. 1, 2 and 3.
Figure 5:
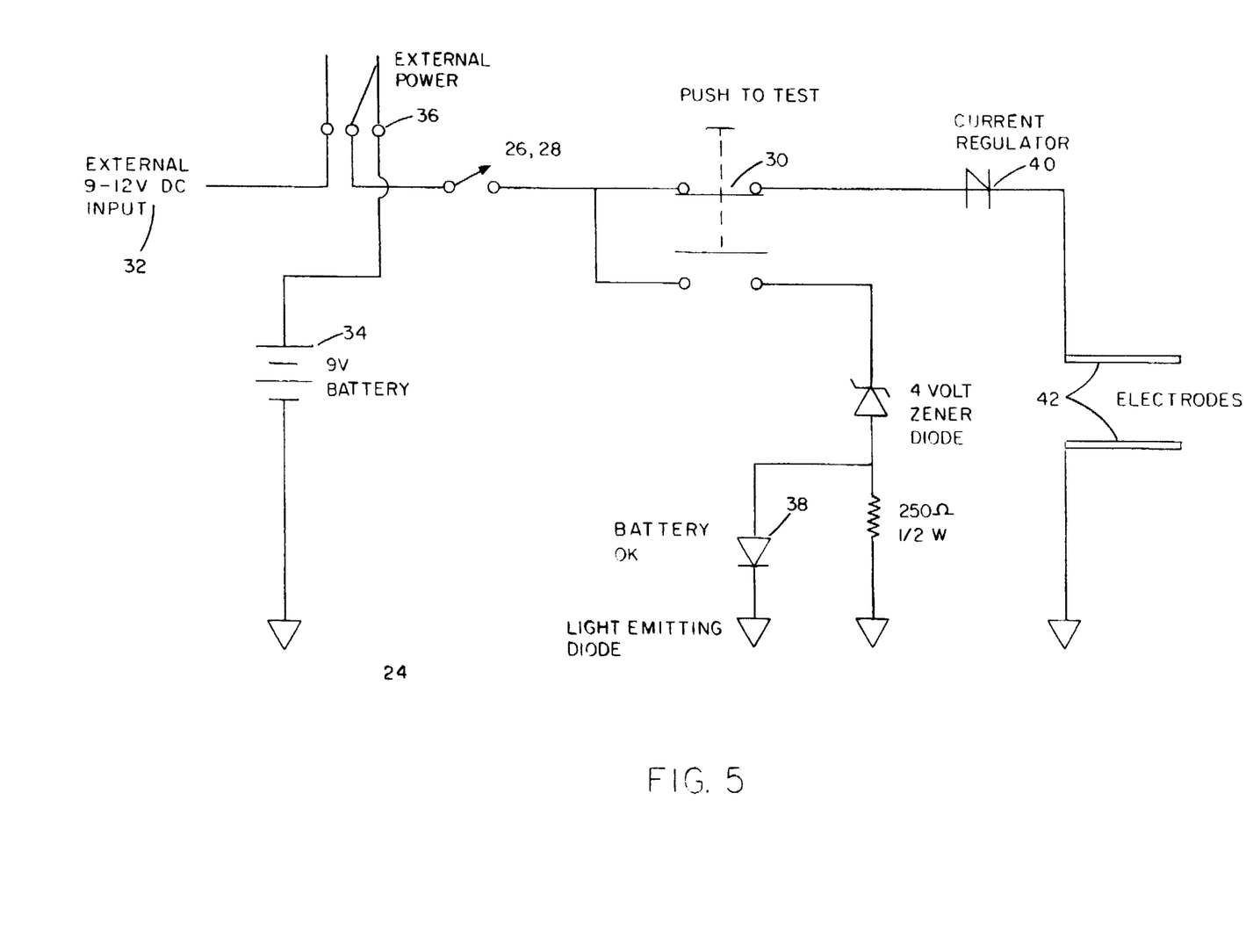
FIG. 5 is a schematic diagram of the circuit used in the apparatus shown in FIGS. 1, 2, 3 and 4.
Figure 6:
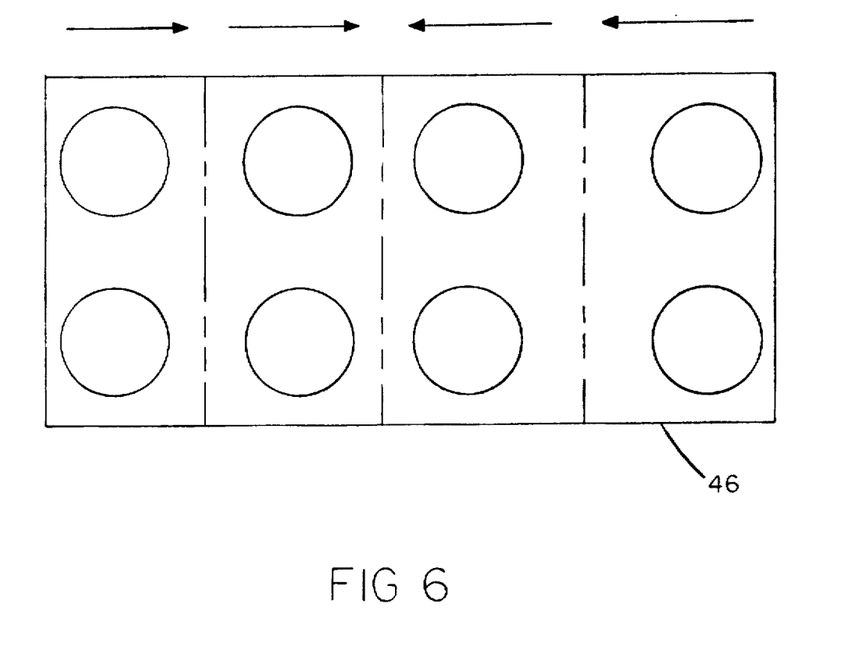
FIG. 6 is a plan view of the adsorbent utilized in the present invention.
Figure 7:
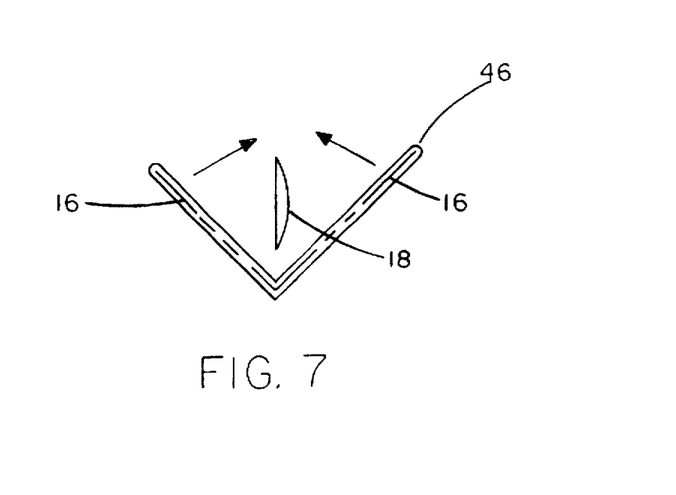
FIG. 7 is a side elevational view of the adsorbent holder of FIG. 6 folded to accommodate the adsorbent and one or more lenses therein.

Suitable control circuitry shown generally as 24 is retained within housing 10 and operates in response to the actuation of control switches 26, 28 and 30. A suitable power source can be a commonly utilized converter or rectifier 32 converting 120 volts ac to operating dc voltages of 28 volts or less or a suitable battery 34 which is commonly available. The power source selection jack 36 connects the internal battery or the external power supply to the balance of the circuit. The off/on switch 26, 28 disconnects the power source from the balance of the circuitry upon actuation. A test switch 30 verifies the active state of the circuit by activating light emitting diode 38 when depressed. A constant current regulator 40 insures a uniform current flow at all times no matter what input voltage variations or solution resistances occur. Electrodes 42 are positioned low in well 14 (FIG. 2) to insure maximum current flow through the solution 44, through the holes in the adsorbent holder, through the adsorbent and around lens 46, 16, 18.

Figure 8:
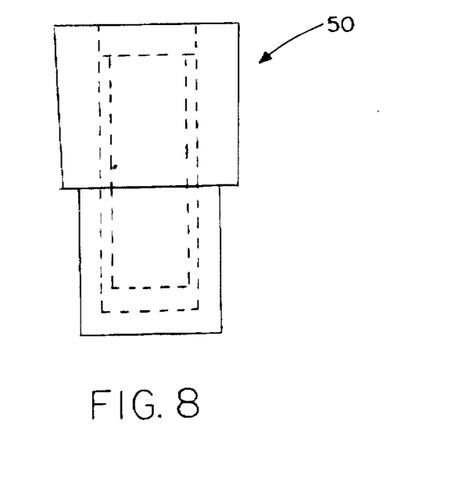
FIG. 8 is a side elevational and sectional view of another embodiment of an apparatus for cleaning contaminants from one or more contact lenses comprising the present invention.
Figure 9:
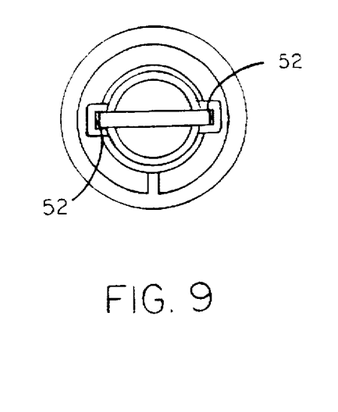
FIG. 9 is a plan view of the embodiments shown in FIG. 8.
Figure 10:
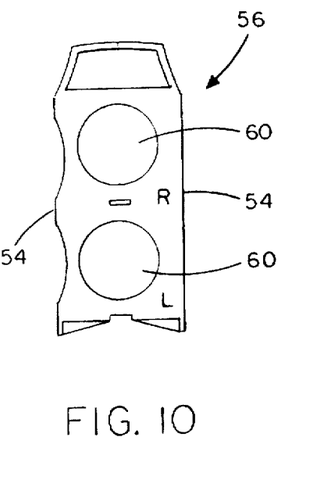
FIG. 10 is a side elevational view of another embodiment of an adsorbent holder utilized in the present invention.
Figure 11:
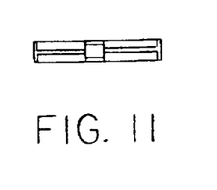
FIG. 11 is a plan view of the holder shown in FIG. 10.
Figure 12:
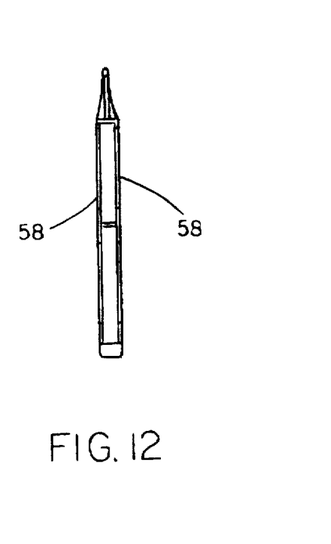
FIG. 12 is an end elevational view of the holder shown in FIGS. 10 and 11.
Figure 13:
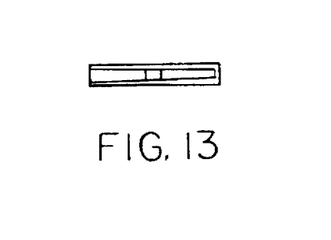
FIG. 13 is a bottom view of the holder shown in FIGS. 10, 11 and 12.

An alternative apparatus utilizing the present inventive concept for cleaning contact lenses is shown in FIGS. 8 and 9. A cleaning well shown generally as 50 having a circular exterior and a cylindrically shaped interior is suitably configured to accommodate and support one or more adsorbents or transfer membranes (not shown) between which are positioned lenses to be cleaned. Well 50 is used with a housing similar to that previously described. The well interior has recesses 52 which engage the edges 54 of adsorbent holder 56 shown generally as 56 in FIGS. 10–13. Ridges 52 hold holder 56 in position and in a manner so as to secure lenses between front and back surfaces 58. These surfaces 58 can be opened to receive the adsorbent material and the lens, then closed to maintain them securely within and thereafter enable holder 56 to be inserted into well 50 and be engaged within recesses 52. Opening 60 in walls 58 give maximum exposure to the adsorbent material and encapsulated lens.

Figure 14:
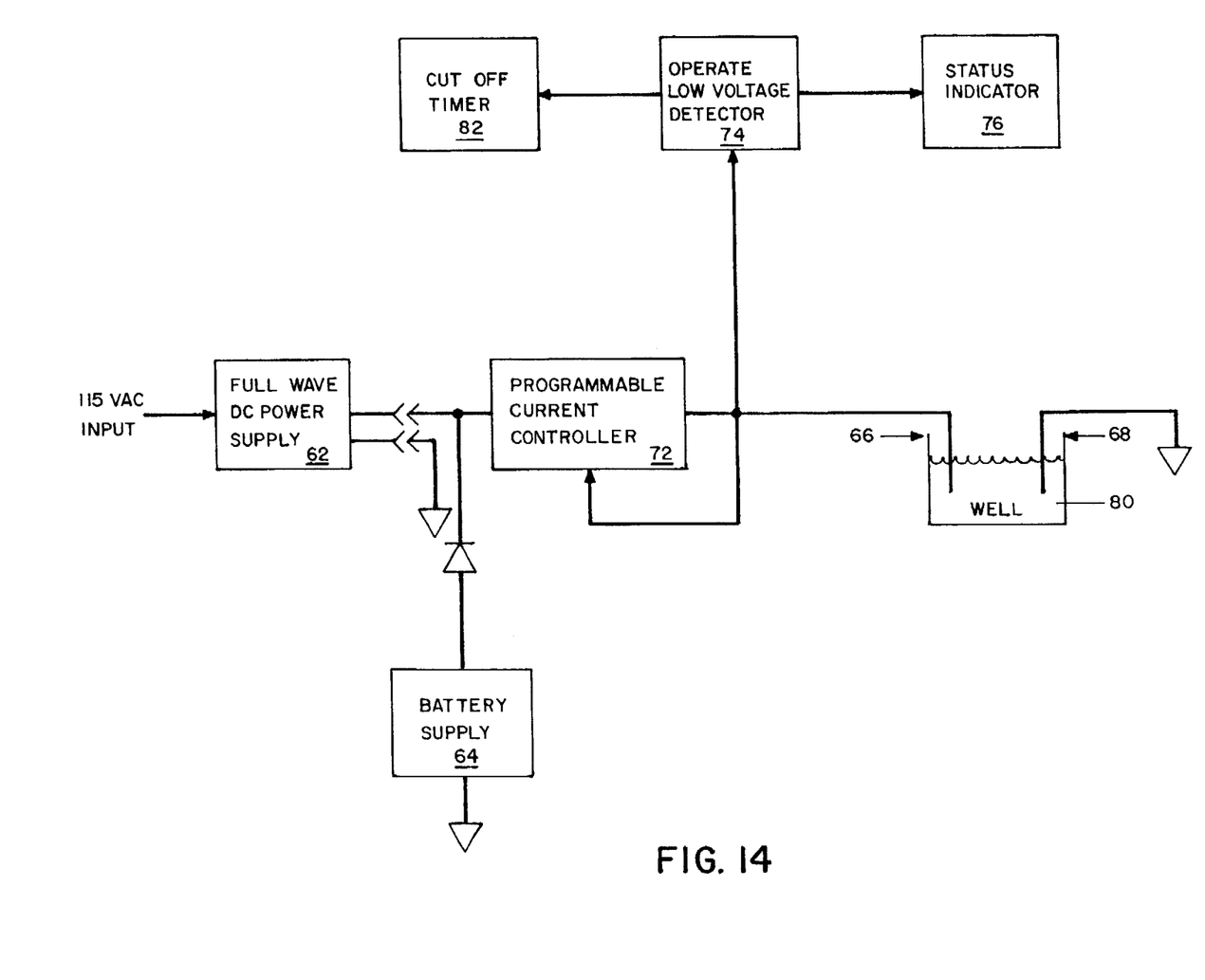
FIG. 14 is a schematic diagram of the circuit used in the embodiment shown in FIGS. 9 and 10.

Alternative and simplified circuitry for the present invention is shown in FIG. 14. The '115 vac line voltage is full wave rectified and filtered in the power supply 62. The rectified output of 28 volts or less can be connected directly to well 50, and the unit can be operated from this supply. However, the '115 vac supply need not be utilized, and the assembly can be operated from the self-contained battery supply 64. In either mode of operation, the "turn-on" command is received from the conduction between electrodes 66, 68. Thus, when cleaning solution 70 is placed in well 50, current begins to flow between electrodes 66, 68, which current is detected in the current control regulator 72, thus turning on the unit.

The programmable current control module 72 maintains the desired current through the cleaning solution 80 independent of the solution resistance as well as through varying battery voltage conditions. The output voltage from the current control module 72 is monitored by the operate/low voltage detector circuit 74. When sufficient power is available from battery supply 64, the operate LED (Light Emitting Diode) 76 illuminates and provides a turn-on command to current control module 72.

When insufficient power is available from battery supply 64, the low voltage LED 76 will illuminate and prevent operation. Also incorporated in the system is a timer circuit 82 which determines the operation time for the entire system. When the lens cleaning cycle is completed, or slightly thereafter, timer circuit 82 activates to de-energize the unit which enhances the life of the battery.

The circuit system is formed from a composite of several integrated circuits that provide high reliability, size and cost savings, and easy replacement of components.

The method for removing contaminants from contact lenses comprising a part of the present invention relies on principles of electroblotting, a process wherein electric current is applied to a substrate which contains ionic material. Individual charged molecules are attracted by and migrate to an electrode or other charged device. In the present invention, the materials removed by the current are proteins and other contaminants retained on contact lenses which, upon the application of current, migrate toward the electrically charged device. The contaminants are then trapped by an adsorbent having an affinity therefor which retains the contaminants. The contaminant laden adsorbent is then discarded. The cleaned lens is then ready for reinsertion by the wearer after rinsing in saline solution.

The method is suitable for use with single or multiple contact lenses immersed in saline or other solution. Suitable lenses include lenses which remain rigid when contacted with water ("hard" contact lenses and "gas-permeable" contact lenses) such as those formed from polymers of polymethyl-methacrylate, silicone methacrylate, methacryloxyalkylsiloxane, methaclylopolsiloxane, methacrylate fluoropolymers, acrylamide, and copolymers thereof, and lenses which form a gel upon water absorption ("soft lenses") such as those formed from hydroxyethyl methacrylate, vinyl dyrrolidone, cellulose acetate butyrate, and copolymers thereof. Lenses which are removed and cleaned daily and lenses which can be worn for weeks or longer between removal and cleaning are suitable.

The choice of an adsorbent or filter used to form the lensadsorbent contact is not critical so long as protein and other contaminants of the lens will adhere. Exemplary adsorbents include polymer membranes, such as PVDP, and cellulosic papers, such as nitrocellulose. Because generally the bulk of contaminants on the lens are proteins, it is preferred that the material comprising the adsorbent contain a free chemical substituent which has a higher affinity for protein, such as an amino, nitro, or carboxyl group. A preferred adsorbent is nitrocellulose membrane, available from Pharmacia Biotechnology located in Piscataway, N.J.

Any configuration wherein the adsorbent is disposed between the lens and the electrically charged device is suitable for use with the method. The adsorbent can be of any shape which permits it to be disposed between the electrically charged device and the lens. It can be flat, folded, arcuate, or multi-arcuate. It can be circular, oval, elliptical, square or any other polygonal shape. The relative positioning of the adsorbent to the lens insures that any contaminant migrating from the lens will immediately be trapped in the adsorbent and will not remain in the solution where potentially it could return to the lens surface. Once trapped in the adsorbent, the adsorbent contaminants are unaffected by the equilibrium phenomenon created by the diffusion gradient and the electrochemical gradient described above and are thus not free to return to the lens surface. Preferably the adsorbent is sized to completely cover the contact lens.

Preferably the adsorbent articles are disposable. Disposability alleviates the need for cleaning the adsorbent after use which use which is preferred since the use of a new adsorbent with each cleaning minimizes the risk of contamination of the lens or infection to the wearer.

The choice of solution is not critical, and any known saline or other suitable solution for cleaning or soaking contact lenses is acceptable. Exemplary saline solutions can include boric acid, sodium borate, sodium chloride, ascorbic acid, and edentate disodium. The pH of the saline solution should be adjusted so that it does not coincide with the isoelectric point of the protein contaminants; otherwise the contaminants would have no electrical charge and thus would not migrate from the lens surface. It is also preferred that the saline solution be buffered to provide a constant pH solution to insure that migrating proteins will maintain their charge during migration. The concentration of the solution is not critical; however, a dilute saline solution is preferred for rapid migration of contaminants as an increased ionic concentration in the saline solution will provide additional ions which competitively carry electric current with contaminant migrants.

The step of applying an electric current to the solution containing the lens can be carried out in any manner which causes current to pass along the surface of the lens itself. Generally, the current is supplied by electrodes immersed in the solution itself like those described previously. Those skilled in the art will appreciate that any means of supplying current to the lens which cause the contaminant thereon to ionize and migrate to a charge device is suitable. When immersed electrodes are used, they are preferably placed so that the current flows over as much of the surface area of the lens as possible. In a preferred orientation, orientation, electrodes are placed on opposite sides of the lens so the current flowing between the electrodes flows substantially perpendicular to an axis extending through the diametric center of the lens. The electrodes are also preferably configured so as to provide a constant current density across the lens area to facilitate removal of protein. Current flow is directed towards the lens.

Manufacturers use a variety of plastic materials in the construction of lenses. The electrical resistance of plastic lenses ranges from 10 million ohms to near infinity. The cleaning process occurs because current flow is around the lens dislodging proteins attached to the lens. At 5 volts applied to a 10 meg ohm resistance, the current through the resistor, would be about 0.5 microamperes. That is about 0.001% of the current recommended to move protein by one adsorbent material manufacturer. Its recommendation is 0.8 milliamps/cm$^2$ of protein removal area which equates to about 4 milliamps for two lenses. Thus the process of removing protein from lenses occurs because electric current is flowing around and over the lenses and is of sufficient magnitude to cause the proteins to move off the lens and into the conductive fluid where movement is then directed toward and against the adsorbent.

The amount of current directed toward the lens in the appropriate solution can be any level which causes protein molecules to migrate toward the oppositely charged electrode. For convenience to the user, the current level should be such that it can be provided by a household power source such as 120 volt electrical outlet supplying a rectifier to obtain 28 volts dc or less or by one or more household batteries. Also, the current level should be sufficiently high that substantially all of the protein migration occurs within a time period in which the wearer can conveniently function without wearing the lenses. A preferred current level which would satisfy these criteria is between about 0.1 and 200 milliamperes with a more preferred current level being under 20 milliamperes. It is also contemplated that the method may be used outside the home by commercial entities that would clean lenses while the wearer waits.

The apparatus and method forming a part of the present invention for removing contaminants from contact lenses has been found to have a broader application. For example, in the medical and laboratory fields, it can be successfully used to sterilize medical and laboratory devices normally sterilizable only through the use of expensive and power-consuming autoclave equipment in very short periods of time at low voltage (28 volts or less) utilizing a current within the range of from 0.1 to 400 milliamperes. Passing a current within this range at such low voltage through a suitable saline or other appropriate solution has been found extremely effective in killing bacteria in surprisingly short periods of time. For example, it has been found effective to pass 10 milliamperes of current through a solution in which are placed contaminated medical instruments for less than 10 minutes to remove essentially all bacteria. It has also been found that lowering current levels to 5 milliamperes or even 1 milliampere only increases the minimum defection time by a factor of three. It appears from test data that exposing contaminated instruments to any low current level at this low voltage is more than adequate to completely disinfect or sterilize those instruments. obviously the use of such low voltage essentially eliminates any electrical hazard.

Figure 15:
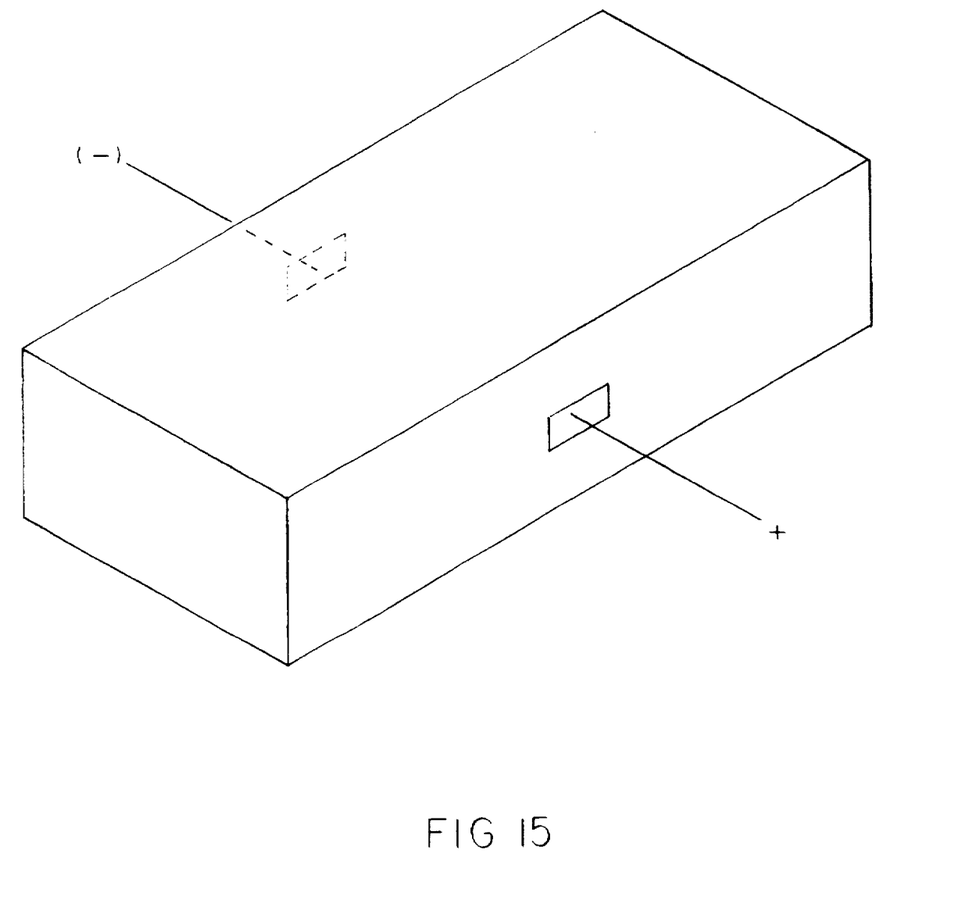
FIG. 15 is a perspective view of a well utilized to sterilize medical and laboratory devices having electrodes and adapted to retain a quantity of saline or other suitable solution all forming the sterilization apparatus of the present invention.

The well used for disinfecting is shown generally in FIG. 15 as 98 wherein electrodes 100, 102 are positioned on the interior surfaces so as to be in direct contact with solution 104 placed therein. A circuit similar to that shown in FIG. 14 is quite acceptable to operate the apparatus.

It will be apparent to those skilled in the art that many variations may be made in the apparatus and method of the present invention without departing from the spirit and scope thereof. While the apparatus and method in accordance with the invention has been specifically exemplified in the foregoing, it will be understood that the example is for the purpose of illustration and that modifications are contemplated. The invention is defined by the following claims with equivalents to the claims to be included therein.

What is claimed is:

1. Apparatus for sterilizing medical instruments and laboratory devices and sterilizing and removing contaminants from contact lenses comprising: a housing including a cleaning well; electrode means positioned within the cleaning well; a power source for supplying electric current to the electrode means positioned within the cleaning well; adsorbent means disposed between the contact lens and the power source; control means for selectively directing current flow to the electrode means; and a predetermined quantity of conductive cleaning solution held within the cleaning well and contiguous with the electrode means completing an electric circuit so that the current flow will pass from the power source through the electrode means, the cleaning solution and solely over the surface of the lens and back to the power source.

2. The apparatus as claimed in claim 1 wherein the power source operates at 28 volts or less.

3. The apparatus as claimed in claim 1 wherein the current is within the range of from 0.1 to 400 milliamperes.

4. The apparatus as claimed in claim 1 wherein the current is less than 20 milliamperes.

5. The apparatus as claimed in claim 2 wherein the current is within the range of from 0.1 to 400 milliamperes.

6. The apparatus as claimed in claim 2 wherein the current is less than 20 milliamperes.

7. Apparatus for sterilizing and removing contaminants from a contact lens comprising: a housing including a cleaning well; electrode means positioned within the cleaning well; holding means insertable within the cleaning well; one or more contact lens held by the holding means; a power source for supplying electric current to the electrode means; adsorbent disposed between the contact lens and the power source; control means for selectively directing current flow through the determined quantity of cleaning solution held within the cleaning well and contiguous with the electrode means, contact lens and adsorbent means completing an electric circuit so that the current flow will pass from the power source through the electrode, the cleaning solution, the adsorbent means and solely over the surface of the contact lens.

8. The apparatus as claimed in claim 7 wherein the power source operates at 28 volts or less.

9. The apparatus as claimed in claim 7 wherein the current is within the range of from 0.1 to 400 milliamperes.

10. The apparatus as claimed in claim 7 wherein the current is less than 20 milliamperes.

11. The apparatus as claimed in claim 8 wherein the current is within the range of from 0.1 to 400 milliamperes.

12. The apparatus as claimed in claim 8 wherein the current is less than 20 milliamperes.

13. The apparatus as claimed in claim 8 wherein the control means includes a test for continuity circuit and a power actuating means.

14. The apparatus as claimed in claim 13 wherein the supporting means includes a configured lower wall within the cleaning well of sufficient dimension to support the contact lens and adsorbent means proximate the electrode means.

15. The apparatus as claimed in claim 14 wherein the electrode means are extended wire elements measuring in length within the range of from 5 mm to 60 mm.

16. The apparatus as claimed in claim 15 wherein the power source is one or more batteries.

17. The apparatus as claimed in claim 15 wherein the power source is a converter for utilizing an alternating current power source.

18. A method of sterilizing and removing contaminants from a contact lens having first and second surfaces comprising: positioning the contact lens, an adsorbent, and an electric current source so that the adsorbent is disposed between the contact lens and the electric current source; immersing the contact lens, the adsorbent, and the electric current source so disposed in a cleaning solution; and directing an electric current from the current source through the cleaning solution, the adsorbent, and solely over the surface of the contact lens so that contaminants carried on the surface of the contact lens migrate to the adsorbent.

19. The method as claimed in claim 18 wherein the electric current source flows at 28 volts or less.

20. A method according to claim 18 wherein the electric current flowing solely over the surface of the contact lens is within the range of from 0.1 to 400 milliamperes.

21. A method according to claim 18 wherein the electric current flowing solely over the surface of the contact lens is under 20 milliamperes.

22. A method of sterilizing and removing contaminants from a contact lens having first and second surfaces comprising: positioning the contact lens, an adsorbent, first and second electrodes, and a power source operating at 28 volts or less so that the adsorbent is disposed between the contact lens and the electric current source and electrodes; immersing the contact lens, the adsorbent, and electric current source and the electrodes so disposed in a cleaning solution; and directing an electric current from the current source and first electrode through the first cleaning solution, the adsorbent and solely over the surface of the contact lens to the second electrode so that contaminants carried by the contact lens migrate to the adsorbent.

23. A method according to claim 22 wherein the power source electric current flowing solely over the surface of the contact lens is within the range of from 0.1 to 200 milliamperes.

24. A method according to claim 22 wherein the electric current flowing over the surface of the contact lens is under 20 milliamperes.

* * * * *